United States Patent
Khandare et al.

(10) Patent No.: US 6,201,161 B1
(45) Date of Patent: *Mar. 13, 2001

(54) METHOD OF REDUCING BENZALDEHYDE OR BENZOTRIHALIDE CONTENT IN A MIXTURE

(75) Inventors: Pravin M. Khandare; Dean R. Lagerwall, both of Amherst; Daniel R. Thielen, Synder, all of NY (US)

(73) Assignee: Occidental Chemical Corporation, Dallas, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/550,458

(22) Filed: Apr. 17, 2000

(51) Int. Cl.$^7$ .............................. C07C 22/00; C07C 17/38
(52) U.S. Cl. .................... 570/196; 570/197; 570/198; 570/211
(58) Field of Search ................................... 570/196, 197, 570/198, 211

(56) References Cited

U.S. PATENT DOCUMENTS 4,105,701 * 8/1978 Larkin ................................. 570/211
4,922,039 * 5/1990 Yamada et al. ...................... 570/211

OTHER PUBLICATIONS

B. F. Filimonov et al., Zh. Obshch. Khim. (1977), 47(7), 1670, titled "Chlorination of Aromatic Aldehydes by Benzotrichloride in the Presence of Iron(III) Chloride".

B. F. Filimonov et al., Zh. Obshch. Khim. (1979), 49(5), 1098–1105, titled "Oxygen–Chlorine Carbenoid Exchange Between Aldehydes and Compounds Containing a Trichloromethyl Group".

* cited by examiner

Primary Examiner—Alan Siegel
(74) Attorney, Agent, or Firm—Richard D. Fuerle; Anne E. Brooks

(57) ABSTRACT

Disclosed is a method of removing about 0.05 to about 20 mole % of a benzaldehyde or benzotrihalide from a mixture with a liquid compound that boils within about −10 to about ±5° C. of the boiling point of the benzaldehyde or benzotrihalide. To the mixture is added a benzotrihalide in an amount about stoichiometric to about 10 mole % in excess of stoichiometric, or, respectively, a benzaldehyde in an amount about stoichiometric with the amount of said benzotrihalide, where said benzaldehyde and said benzotrichloride react to form a benzalhalide and a benzoylhalide. The product mixture is distilled to isolate the products.

20 Claims, No Drawings

METHOD OF REDUCING BENZALDEHYDE OR BENZOTRIHALIDE CONTENT IN A MIXTURE

BACKGROUND OF THE INVENTION

This invention relates to a method of reducing the benzaldehyde or benzotrihalide content in a mixture with a compound that boils at about the same temperature. In particular, it relates to adding a benzotrihalide or a benzaldehyde to the mixture to react with the benzaldehyde or a benzotrihalide, respectively, in order to form products having a greater difference in boiling point and therefore are more easily separated by distillation.

When 2,4-dichlorotoluene (2,4-DCT) is reacted with chlorine in the presence of ultraviolet light a mixture of 2,4-dichlorobenzylchloride (2,4-DCBC) and 2,4-dichlorobenzalchloride (2,4-DCBAC) can be made. If the reaction mixture is exposed to moisture, however, some of the 2,4-DCBAC is hydrolyzed to 2,4-dichlorobenzaldehyde (2,4-DCBAL). When the product mixture is distilled, the 2,4-DCBC contains 2,4-DCBAL due to a relative volatility of close to one (boiling points) =248 and 250° C., respectively). The presence of 2,4-DCBAL in the 2,4-DCBC is not acceptable for uses such as making stabilizers, but separation of the 2,4-DCBAL by distillation is time-consuming and costly.

When p-chlorotoluene (PCT) is chlorinated, a mixture of p-chlorobenzalchloride (PCBAC) and p-chlorobenzotrichloride (PCBTC) can be made. Separating the PCBAC by distillation is difficult due to the low relative volatility between PCBAC and PCBTC, reduces distillation yield.

SUMMARY OF THE INVENTION

We have found that a benzaldehyde can be separated from a mixture with a desired compound that boils at about the same temperature by reacting the benzaldehyde with a benzotrihalide. That reaction forms a benzalhalide and a benzoylhalide, which have substantially different boiling points than the desired compound, so the desired compound can be more easily separated by distillation.

Similarly, a benzotrihalide can be more easily separated from a compound that boils at about the same temperature by reacting the benzotrihalide with a benzaldehyde to form a benzalchloride and a benzoylchloride, which have significantly different boiling points.

DESCRIPTION OF THE PREFERRED EMBODIMENTS

This invention is applicable to benzotrihalides and benzaldehydes having the respective general formulas:

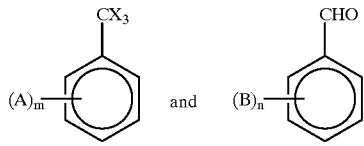

where each A is independently selected from halogen, $CF_3$, R, or OR, each B is independently selected from halogen, $CF_3$, or R, R is alkyl from $C_1$ to $C_{10}$ or aryl from $C_6$ to $C_{12}$, m is 0 to 3, and n is 0 to 2. Preferably, A is Cl or $CF_3$, B is Cl, R is alkyl from $C_1$ to $C_6$, m is 0 to 2, and n is 0 or 1. Examples of benzotrihalides that can be used include benzotrichloride (BTC), o-chlorobenzotrichloride (OCBTC), —-chlorobenzotrichloride (MCBTC), p-chlorobenzotrichloride (PCBTC), 2,4-dichlorobenzotrichloride (2,4-DCBTC), and 3,4-dichlorobenzotrichloride (3,4-DCBTC), 2,5-dichlorobenzotrichloride (2,5-DC BTC). The preferred benzotrihalides are 2,4-DCBTC, 3,4-DCBTC, OCBTC, MCBTC, and PCBTC. Examples of benzaldehydes that can be used include benzaldehyde (BAL), o-chlorobenzaldehyde (OCBAL), m-chlorobenzaldehyde (MCBAL), and p-chlorobenzaldehyde (PCBAL). The preferred benzaldehydes are BAL and OCBAL.

The compound to be removed, either the benzaldehyde or the benzotrihalide, constitutes about 0.05 to about 20 mole %, and more typically about 1 to about 5 mole %, of a mixture with a compound that has a boiling point within −10 to +5° C. of the boiling point of the benzotrihalide or benzaldehyde, and preferably within about −5 to about +5° C. of that boiling point. Typically, the other compound in the mixture will be the corresponding benzotrihalide, benzaldehyde, benzylhalide, benzalhalide, or benzoylhalide.

As an example, 2,4-DCBAL can be separated from a mixture of 2,4-DCBC and 2,4-DCBAC by adding 2,4-DCBTC, which reacts with the 2,4-DCBAL to form additional 2,4-dichlorobenzalchloride (2,4-DCBAC) and 2,4-dichlobenzoylchloride (2,4-DCBOC). Since the 2,4-DCBAC and the 2,4-DCBOC are higher boiling than the 2,4-DCBC, the 2,4-DCBC can now be more easily isolated by distillation.

As another example, PCBAC can be more easily separated from a mixture with PCBTC by reacting the PCBTC with PCBAL to form additional PCBAC and p-chlorobenzoylchloride (PCBOC). The PCBOC is higher boiling than the PCBAC.

To remove a benzaldehyde from a mixture, the amount of benzotrichloride added should be about stoichiometric with the amount of benzaldehyde present in the mixture up to about 10 mole % in excess of stoichiometric; preferably, the amount of benzotrichloride added is about 1 to about 5 mole % in excess of stoichiometric. If a benzaldehyde is added to a mixture to remove a benzotrihalide, the amount of benzaldehyde used should be at least stoichiometric with the amount of benzotrichloride in the mixture. To simplify the separation of products, it is preferable to use the corresponding benzaldehyde and benzotrihalide. The benzotrihalide or benzaldehyde can be added before, during, or after a reaction that forms the benzaldehyde or benzotrihalide, respectively.

The reaction between the benzaldehyde and the benzotrihalide occurs at room temperature; higher temperatures due to the accumulation of reaction heat or to external heating will accelerate the reaction. No catalyst is needed, though about 0.01 to about 1 wt % of a Lewis acid catalyst, such as zinc chloride or ferric chloride, can be used to accelerate the reaction if desired. Before distilling, the reaction should be held at an elevated temperature for a period of time to permit the reaction between benzaldehyde and benzotrichloride to occur. The reaction time, reaction temperature, and catalyst level directly influence the reaction rate and, therefore, the level of benzaldehyde or benzotrichloride in the mixture.

The following examples further illustrate this invention:

EXAMPLE 1

To prepare a test mixture, 2.32 g (0.27 wt %) of 2,4-DCBAL was added to 860 g of a 85:15 wt % mixture of 2,4-DCBC:2,4-DCBAC. Distillation in a 30-plate×1" ID Oldershaw column at reflux ratios ranging from 10:1 to 25:1 over 11.25 hours resulted in a loss of 148.4 g of the desired 2,4-DCBC product in the foreshot due to 2,4-DCBAL contamination. The final distillate contained 0.51% (GC area %) 2,4-DCBAL. When the distillation was repeated, but with 26.6 g 2,4-DCBTC (11.5 wt excess or 7.6 molar excess based on 2,4-DCBAL), the 2,4-DCBAL level in the distillate was reduced to a non-detectable level. Only 26.5 g of contaminated 2,4-DCBC was collected in the foreshot over 36 hours, of which 12.75 hrs was the reaction time at 160° C. before the distillation was started.

EXAMPLE 2

To prepare a test mixture, 2.44 9 (0.28 wt %) of 2,4-DCBAL was added to 860 g of a 85:15 wt % mixture of 2,4-DCBC:2,4-DCBAC. In addition, 11.52 g of 2,4-DCBTC (3.12 molar excess based on 2,4-DCBAL) and 0.8589 g (1000 ppm) of zinc acetate catalyst were added to the reboiler. To induce reaction in the reboiler, the mixture was held at 160° C. for approximately 3 hours. The 2,4-DCBAL level was reduced and only 66 g of 2,4-DCBC was contaminated with 2,4-DCBAL, which was collected in the foreshot over 7.65 hours at 20:1 reflux ratio; 2,4-DCBAL was not detectable in the final distillate.

EXAMPLE 3

A 1283 g mixture containing 0.38 gmoles PCBC, 4.45 gmoles PCBAC and 1.53 gmoles PCBTC was reacted with 1.774 BAL in the presence of zinc acetate catalyst at 160° C. The reaction product analyses showed 1.77 gmoles benzalchloride (BAC), 1.214 gmoles PCBOC, 4.37 gmoles PCBAC and 0.19 gmoles PCBAL. Upon distillation in a 30-plate×1" Oldershaw column, 99.81% pure PCBAC was recovered, resulting in 81% yield.

We claim:

1. A method of removing about 0.05 to about 20 mole % of a benzaldehyde or benzotrihalide from a mixture with a liquid compound that boils within about −10 to about 5° C. of the boiling point of said benzaldehyde or benzotrihalide comprising
   (A) adding to said mixture a benzotrichloride in an amount about stoichiometric to about 1 mole % in excess of stoichiometric with the amount of said benzaldehyde or, respectively, adding to said mixture a benzaldehyde in an amount about stoichiometric with the amount of said benzotrihalide, whereby said benzotrihalide and said benzaldehyde react to form a benzalhalide and a benzoylhalide; and
   (B) isolating said liquid compound by distillation.
2. A method according to claim 1 wherein said mixture comprises a benzaldehyde and the corresponding benzylchloride.
3. A method according to claim 2 wherein said benzylchloride is 2,4-dichlorobenzylchloride.
4. A method according to claim 2 wherein said benzylchloride is 3,4-dichlorobenzylchloride.
5. A method according to claim 2 wherein said benzylchloride is benzylchloride.
6. A method according to claim 2 wherein said benzylchloride is metachlorobenzylchloride.
7. A method according to claim 2 wherein said benzylchloride is parachlorobenzylchloride.
8. A method according to claim 2 wherein said benzylchloride is a trifluoromethylbenzylchloride.
9. A method according to claim 2 wherein said benzylchloride is formed by chlorinating the corresponding toluene.
10. A method according to claim 1 wherein said mixture comprises a benzotrichloride and the corresponding benzalchloride.
11. A method according to claim 10 wherein said benzotrihalide is benzotrihalide.
12. A method according to claim 1 wherein no Lewis acid catalyst is used.
13. A method according to claim 1 wherein about 0.01 to about 1 wt % of a zinc chloride catalyst is added.
14. A method of making a benzylchloride comprising
    (A) chlorinating toluene having the general formula

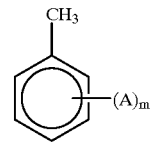

to produce a mixture of the corresponding benzylchloride and the corresponding benzalchloride, where each A is independently selected from Cl, $CF_3$, or alkyl from $C_1$ to $C_6$ and m is 0 to 2, where water reacts with about 1 to about 5 mole % of said benzalchloride to form the corresponding benzaldehyde;
    (B) adding the corresponding benzotrichloride to said mixture in an amount about 1 to about 5 mole % in excess of a stoichiometric amount, whereby said corresponding benzotrichloride reacts with said corresponding benzaldehyde to form a mixture of said benzalchloride and the corresponding benzoylchloride; and
    (C) distilling said benzylchloride from said mixture.
15. A method according to claim 14 wherein A is chlorine.
16. A method according to claim 14 wherein said toluene is 2,4-dichlorotoluene.
17. A method according to claim 14 wherein chlorine gas is used to chlorinate said toluene.
18. A method of making a benzalchloride comprising
    (A) chlorinating toluene having the general formula

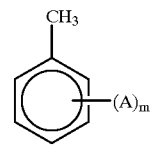

to produce a mixture of the corresponding benzalchloride and the corresponding benzotrichloride, where each A is independently selected from Cl, $CF_3$, or alkyl from $C_1$ to $C_6$ and m is 0 to 2;
    (B) adding the corresponding benzaldehyde to said mixture in an amount about 1 to about 5 mole % in excess of a stoichiometric amount, whereby said corresponding benzotrichloride reacts with said corresponding benzaldehyde to form a mixture of said benzalchloride and the corresponding benzoylchloride; and
    (C) distilling said benzalchloride from said mixture.
19. A method according to claim 18 wherein A is chlorine.
20. A method according to claim 18 wherein m is 0.

* * * * *